US010739352B2

(12) United States Patent
Percival et al.

(10) Patent No.: US 10,739,352 B2
(45) Date of Patent: Aug. 11, 2020

(54) DIAGNOSIS AND TREATMENT OF WOUND INFECTION WITH PROCALCITONIN AS DIAGNOSTIC MARKER

(75) Inventors: Steven Lane Percival, Chester (GB); Philip Godfrey Bowler, Cheshire (GB); Samantha Alison Jones, Deeside (GB); Sarah Anne Welsby, Deeside (GB)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 0 days.

(21) Appl. No.: 12/743,633

(22) PCT Filed: Nov. 20, 2008 (Under 37 CFR 1.47)

(86) PCT No.: PCT/GB2008/003893
§ 371 (c)(1),
(2), (4) Date: May 19, 2010

(87) PCT Pub. No.: WO2009/066075
PCT Pub. Date: May 28, 2019

(65) Prior Publication Data
US 2011/0039342 A1    Feb. 17, 2011

(30) Foreign Application Priority Data
Nov. 20, 2007   (GB) .................................. 0722729.1

(51) Int. Cl.
| G01N 33/68 | (2006.01) |
| A61L 15/16 | (2006.01) |
| A61L 15/22 | (2006.01) |
| A61L 15/42 | (2006.01) |

(52) U.S. Cl.
CPC .......... *G01N 33/6863* (2013.01); *A61L 15/22* (2013.01); *A61L 15/42* (2013.01); *G01N 2333/5753* (2013.01); *G01N 2800/26* (2013.01)

(58) Field of Classification Search
CPC .................... G01N 2800/26; G01N 2333/5753
See application file for complete search history.

(56) References Cited

U.S. PATENT DOCUMENTS

| 6,426,227 | B1 | 7/2002 | Kritzman et al. | |
| 6,451,311 | B2 * | 9/2002 | Althaus et al. ............ | 424/158.1 |
| 6,478,938 | B1 | 11/2002 | Paek et al. | |
| 2003/0194752 | A1 * | 10/2003 | Anderson et al. ............ | 435/7.2 |
| 2008/0118911 | A1 * | 5/2008 | Hermann ......... | G01N 33/54333 435/5 |

FOREIGN PATENT DOCUMENTS

| GB | 2430031 | 3/2007 |
| WO | WO-97/25622 | 7/1997 |
| WO | WO-00/08203 | 2/2000 |
| WO | WO-00/65083 | 11/2000 |
| WO | WO2004/086043 | 10/2004 |
| WO | WO 2006/024466 A2 * | 3/2006 |

OTHER PUBLICATIONS

Jeandrot, A. et al. "Serum procalcitonin and C-reactive protein concentrations to distinguish mildly infected from non-infected diabetic foot ulcers: a pilot study," Diabetologia (2008) 51:347-352; Published online: Oct. 13, 2007.*
Mueller, B. et al. "Ubiquitous Expression of the Calcitonin-I Gene in Multiple Tissues in Response to Sepsis," The Journal of Clinical Endocrinology & Metabolism, 2001, 86, 396-404.*
Machine translation of WO 97/25622 by Claude Bohoun and published Jul. 17, 1997; translation obtained on Feb. 4, 2015 from www.wipo.int.*
Fleischhack, G. et al. "Procalcitonin in paediatric cancer patients: its diagnostic relevance is superior to that of C-reactive protein, interleukin 6, interleukin 8, soluble interleukin 2 receptor and soluble tumour necrosis factor receptor II," British Journal of Haematology, 2000, 111, 1093-1102.*
Schuetz, P. et al. "Biomarkers to improve diagnostic and prognostic accuracy in systemic infections," Current Opinion in Critical Care; vol. 13, Issue 5, pp. 578-585 (Oct. 2007).*
Bergamini, T.M. et al. "Combined topical and systemic antibiotic prophylaxis in experimental wound infection," Am J Surg. Jun. 1984; 147(6):753-6. (Year: 1984).*
Ostermann, P.M. et al. "The role of local antibiotic therapy in the management of compound fractures." Clin Orthop Relat Res. Oct. 1993; (295):102-11. (Year: 1993).*
Brahms PCT-Q. Immunochromatografic test for the determination of PCT (procalcitonin) in serum and plasma. Instruction Manual (Version R07en). pp. 1-2. May 19, 2004 (Year: 2004)*
Maruna, P. et al. "Procalcitonin in the diagnosis of postoperative complications," Sb Lek. 2002; 103(2): 283-95. Abstract only (Year: 2002).*
Fivenson, David P. et al., "Chemokine and inflammatory cytokine changes during chronic wound healing" Wound Repair and Regeneration, vol. 5, No. 4, Oct. 1997, pp. 310-322.
Schneider, Hans-Gerhard et al., "Procalcitonin for the clinical laboratory: a review" Pathology, vol. 39, No. 4, Aug. 2007, pp. 383-390.

(Continued)

*Primary Examiner* — Christopher Adam Hixson
*Assistant Examiner* — Michelle Adams
(74) *Attorney, Agent, or Firm* — Taft Stettinius & Hollister LLP; Ryan O. White

(57) ABSTRACT

A method of diagnosis or prediction of infection of a mammalian wound, said method comprising the step of detecting the presence of a cytokine selected from the group comprising procalcitonin, amino procalcitonin (N-ProCT), eotaxin, granulocyte macrophage colony stimulating factor (GM-CSF), interleukins IB monocyte chemotactic protein-1 (MCP-1), macrophage inflammatory protein-1 alpha (MIP-1a), regulated upon activation normal T expressed and secreted (RANTES) in fluid taken from the wound. Also claimed is the device for use in the method.

20 Claims, No Drawings

(56) References Cited

OTHER PUBLICATIONS

Forsberg, JA and Elster, E, "Cytokine expression correlates with wound dehiscence in wartime extremity injuries" Journal of Surgical Research, vol. 137, No. 2, Jan. 2007, pp. 208-209.
Database CA [Online] Chemical Abstracts Service, Jiang, Qian et al., "The detection and significance of serum eotaxin in children with respiratory adenovirus infection" STN Database Accession No. 145:311772, (2005).
Ellmark, Peter et al., "Identification of protein expression signatures associated with Helicobacter pylori infection and gastric adenocarcinoma using recominant antibody microarrays" Molecular and Cellular Proteomics, vol. 5, No. 9, pp. 1638-1646, (2006).
Papadopoulos, N G et al., "Rhinovirus infection up-regulates eotaxin and eotaxin-2 expression in bronchial epithelial cells" Clinical and Experimental Allergy, vol. 31, No. 7, Jul. 2001, pp. 1060-1066.
Forsberg et al., The Journal of Bone and Joint Surgery, 2008, vol. 90, pp. 580-588.
Canadian Patent Application No. 2756566 Office Action dated Nov. 15, 2016.
Brahms PCT-Q, Immunochromatografic test for the determination of PCT (procalcitonin) in human serum and plasma. Aug. 29, 2007, pp. 1-4.
Canadian Patent Application No. 2706080 Office Action dated Sep. 14, 2017.
Brahms PCT-Q, Immunochromatografic test for the determination of PCT (procalcitonin) in human serum and plasma. Aug. 29, 2007, 10-4.
International Search Report; European Patent Office; International Application No. PCT/GB2008/003893; dated Jul. 14, 2009; 6 pages.
Australian First Examination Report; Australia Patent Office; Australian Patent Application No. 2008327712; dated Aug. 13, 2013; 5 pages.
Australian Second Examination Report; Australia Patent Office; Australian Patent Application No. 2008327712; dated Sep. 29, 2014; 3 pages.
Canadian Office Action; Canadian Intellectual Property Office; Canadian Patent Application No. 2,706,080; dated Dec. 2015; 5 pages.
Canadian Office Action; Canadian Intellectual Property Office; Canadian Patent Application No. 2,706,080; dated Nov. 18, 2016; 4 pages.
Canadian Office Action; Canadian Intellectual Property Office; Canadian Patent Application No. 2,706,080; dated Sep. 14, 2017; 6 pages.
Canadian Office Action; Canadian Intellectual Property Office; Canadian Patent Application No. 2,706,080; dated May 15, 2018; 4 pages.
Canadian Office Action; Canadian Intellectual Property Office; Canadian Patent Application No. 2,706,080; dated Feb. 5, 2019; 7 pages.
European Office Action; European Patent Office; European Application No. 08852268.5; dated Mar. 6, 2014; 3 pages.
European Office Action; European Patent Office; European Application No. 08852268.5; dated Aug. 7, 2014; 3 pages.

* cited by examiner

DIAGNOSIS AND TREATMENT OF WOUND INFECTION WITH PROCALCITONIN AS DIAGNOSTIC MARKER

The present invention relates to monitoring patients for the onset or development of wound infection, by detecting the presence and/or level of a marker associated with sub-clinical or clinical infection in a wound. The marker may be a precursor to a hormone associated with sub-clinical or clinical infection in a wound, especially in wound fluid or maybe a cytokine.

In mammals, dermal injury triggers an organised complex cascade of cellular and biochemical events that result in a healed wound. Wound healing is a complex dynamic process that results in the restoration of anatomic continuity and function; an ideally healed wound is one that has returned to normal anatomic structure, function and appearance.

Chronic wounds are naturally colonised with bacterial flora. Infection of wounds by bacteria delays the healing process, since bacteria produce enzymes and toxins and also compete for nutrients and oxygen with macrophages and fibroblasts whose activities are essential for the healing of the wound. Infection is therefore a manifestation of a disturbed host/bacteria equilibrium in favour of the invading bacteria. This elicits a systemic septic response, and also inhibits the multiple processes involved in wound healing. The granulation phase of healing will only begin after the infection has subsided.

In clinical practice, a diagnosis of infection is based on the presence of local pain, heat, swelling, discharge and redness, although many clinical indicators, such as inflammation and discharge have a low predictive value of infection in wounds. Diagnosis of infection is commonly confirmed by microbiological analysis of wound samples which may take several days to complete. Delay in diagnosis of infection can delay the administration of antimicrobial therapy and may increase the risk of developing sepsis. Conversely a rapid diagnosis of the absence of infection reduces the inappropriate use of antibiotic therapy.

There therefore remains a need in the art for a method for the early diagnosis of wound infection, and for devices and wound dressings for use in carrying out such methods.

Certain cytokines are markers for bacterial inflammation. For example procalcitonin is the peptide precursor of calcitonin. The release of procalcitonin from tissues is induced directly via the presence of bacteria.

The present inventors have made the surprising discovery that certain cytokines are indicative of wound infection and that the level of cytokine is correlated to the level of infection in the wound. Further the present inventors have discovered that certain cytokines are found in the wound fluid of sub-clinically or clinically infected wounds.

The present invention relates to markers to predict or confirm patients for wound infection. The marker is preferably a cytokine and may be a precursor to a hormone. The cytokine may be detected by the use of an assay.

Accordingly a first aspect of the present invention provides a method of diagnosis or prediction of infection of a mammalian wound, said method comprising the step of detecting the presence of a cytokine selected from the group comprising procalcitonin, amino procalcitonin (N-ProCT), eotaxin, granulocyte macrophage colony stimulating factor (GM-CSF), interleukins 1B monocyte chemotactic protein-1 (MCP-1), macrophage inflammatory protein-1 alpha (MIP-1a), regulated upon activation normal T expressed and secreted (RANTES). In an embodiment, the method is an in vitro method carried out on a sample of wound fluid that has been taken from the wound.

An advantage of the detection of procalcitonin is that an elevated level in blood has been shown to occur only in response to inflammation resulting from bacterial or fungal infection. Viral infections do not cause procalcitonin levels to rise.

Accordingly, in a second aspect the present invention provides a method of diagnosis or prediction of infection of a mammalian wound, said method comprising the step of detecting the presence of at least one of the markers selected from the group comprising procalcitonin, amino procalcitonin (N-ProCT), eotaxin, granulocyte macrophage colony stimulating factor (GM-CSF), interleukins 1B monocyte chemotactic protein-1 (MCP-1), macrophage inflammatory protein-1 alpha (MIP-1a), regulated upon activation normal T expressed and secreted (RANTES) in a sample of wound fluid taken from said wound. In an embodiment, the method is an in vitro method carried out on a sample of wound fluid that has been taken from the wound.

The finding that at least one of the markers is present in a wound indicates that local infection is evident. The marker is detected typically by using an assay that generates a colour change in a test strip. The intensity of colour generated is directly proportional to the marker concentration in the sample. A diagnostic kit such as BRAHMS PCT-Q may be used to detect the marker. For example for procalcitonin a baseline level is less than 0.05 ng/ml in a normal healthy subject. After the onset of infection the level of procalcitonin can rise up to 1000 times the initial level within 2 to 3 hours of onset of infection and then continue to increase over the following 24 hours. Typically, a sample of wound fluid containing procalcitonin in the region of $\geq 0.5$ and $\leq 2$ ng/ml indicates that bacterial infection is highly likely. Preferably, the test strip is accompanied by a chart of reference colours where the intensity of the colour generated on the test strip correlates with the level of marker present. Preferably, with procalcitonin the assay has reference bands at $\leq 0.5$ ng/ml, 0.5 ng/ml, $\geq 2$ ng/ml and $\geq 10$ ng/ml.

Typically, a sample of wound fluid containing procalcitonin in the region of >2 ng/ml indicates an infected wound and $\geq 10$ ng/ml indicates a highly infected wound. The test strip will preferably have a positive test band that shows that the test is complete to avoid doubt where no marker is detected.

Alternatively other methods may be used to detect or measure the concentration of the marker. Suitable methods include the use of diagnostic equipment such as VIDAS BRAHMS PCT, KRYPTOR and BRAHMS PCT sensitive LIA which use antibodies specific to the marker which bind and produce a fluorescent or luminescent signal proportional to the level of marker present. The results of these tests are typically analysed by diagnostic software. The analysis of a sample from the wound is carried out by taking a sample of the patients' wound fluid. The fluid is centrifuged and then applied to the test and measured either semi-quantitatively or quantitatively using a rapid kit or laboratory based equipment.

Using the results of the assay, the presence and severity of the infection can be estimated and the course of treatment decided based on this. The success of treatments can also be monitored by repeating the test for example every 12 hours.

The term "wound fluid" refers to any wound exudate or other fluid (substantially not including blood) that is present at the surface of the wound or that is removed from the wound surface by aspiration, absorption or washing. The term "wound fluid" does not refer to blood or tissue plasma remote from the wound site.

In a second embodiment the invention comprises a diagnostic device for use in diagnosis or prediction of infection of a mammalian wound by measuring the level of a cytokine selected from the group comprising procalcitonin, amino procalcitonin (N-ProCT), eotaxin, granulocyte macrophage colony stimulating factor (GM-CSF), interleukins 1B monocyte chemotactic protein-1 (MCP-1), macrophage inflammatory protein-1 alpha (MIP-1a), regulated upon activation normal T expressed and secreted (RANTES) by measuring the presence and level of the cytokine in the wound fluid, wherein the device comprises a binding partner for the cytokine.

The devices of the present invention can be in the form of a wound dressing comprising the binding partner for the cytokine which on absorption of fluid from the wound form a complex to give a colour change indicative of the presence and level of the cytokine in the wound fluid. Alternatively the devices of the present invention can be in the form of a test kit comprising a pipette, a test strip and a colour scale or a dip stick for dipping in the wound and a colour scale.

The device is used to determine the presence and level of cytokine present in the wound fluid. According to the level detected a suitable diagnosis can be made and an appropriate treatment given.

The invention will now be illustrated by the following non-limiting examples.

EXAMPLE 1

A sample of wound fluid was taken from a wound located on the lower hind limb of a horse. The wound fluid was tested using BRAHMS PCT Q kit which comprises a pipette, a lateral flow test strip and a colour scale and can indicate the presence and level of procalcitonin in the wound fluid. The test consisted of the application of 200 μl of wound fluid onto the test area of the strip. The formation of an antibody-procalcitonin complex sandwich on the test strip generated a visible red band on the strip, the intensity of which was used to determine the level of procalcitonin using a semi-quantitative colour scale. The band indicated that the wound fluid contained procalcitonin in the region of $\geq 0.5$ and $\leq 2$ ng/ml. Using the test kit guidelines, the level of procalcitonin indicated that bacterial infection was highly likely and therefore local and systemic antimicrobial therapy was administered.

EXAMPLE 2

Twenty eight client-owned horses admitted to the Philip Leverhulme Large Animal Hospital at Leahurst, University of Liverpool, Wirral for either chronic or acute wound treatment were evaluated. The horses ranged between 1 and 19 years of age and included eleven mares, eleven geldings, four fillies and two colts. The wound exudate samples were collected from trauma, surgical and burn wounds.

Reagent Preparation

Sterile Saline: Saline was prepared at a concentration of 0.9% with distilled water and autoclaved at 121° C.

Normal Equine Serum: Sterile equine serum was obtained from Sigma-Aldrich Ltd (Poole, Dorset). Lot: 26H4612; Expiry date: July 2013. The serum was aliquoted, aseptically and frozen at −20° C. until required.

Methods

Wound exudate collection: Wound exudates were collected during dressing changes and centrifuged for 30 minutes at 2000 rpm in order to remove any blood cells. One set of wound exudates were evaluated immediately. The second set of wound exudates were collected and immediately frozen at −20° C. Frozen samples were thawed for 10 minutes at 37° C. and gently vortexed for 30 seconds before applying to the PCT kit.

Procalcitonin (PCT) analysis: PCT analysis was carried out using the BRAHMS PCT-Q kit. This is a semi-quantitative test and takes approximately 30 minutes to obtain a result. Its reading range is between 0.5 ng/ml and 10 ng/ml, and it can be performed in the laboratory or clinic.

Six drops of wound exudate were pipetted into the concave cavity of the kit (~200 μl) and incubated at room temperature for 30 minutes. After which, the PCT concentration was determined by comparing the colour intensity of the test band with the colour blocks of the reference card supplied with the kit. If no control band appears on the card the test is considered to be invalid.

Results

Normal horse serum (n=3) and sterile saline 0.9% (n=3) were tested using the PCT-Q test and both gave negative results. Both displayed a negative result with only the positive test band visible.

Fresh wound exudate PCT concentrations in eleven horses with chronic or acute wounds were evaluated (Table 1). Table 1 also includes information on the breed, age, sex, type of wound and signs of infection. The centrifuged exudate was tested immediately after being removed from the wound.

Of the 11 exudate samples tested, five gave a result of <0.5 ng/ml (four of these were trauma wounds and one an open chest wound), three samples gave a negative result and two were not tested due to the wound exudates being too viscous despite being centrifuged. Finally, wound exudate from a burn wound was tested and this gave a PCT result of >2.0 ng/ml.

Seventeen wound exudate samples were tested after being frozen at −20° C. (Table 2). Three of these samples (from acute wounds) revealed a PCT result of <0.5 ng/ml. A further eight acute wound samples displayed a negative result (i.e. no band on the test kit). In addition five cases presented wounds that ranged from a few days to three weeks of age and each of these displayed a result of 0.5 ng/ml PCT but there were no visible signs of clinical infection. Finally, the most recent case was from a trauma hock wound that was clearly infected i.e. there was a lot of pus and the wound had a highly pungent odour. This scored <2.0 ng/ml PCT. As a comparison further wound exudates were collected and frozen at −20° C. The test was carried out as above.

In the twenty eight wound exudates that were sampled 46% were negative (from acute wounds), 29% scored <0.5 ng/ml (early trauma wounds), 18% scored 0.5 ng/ml (trauma wounds of a longer duration) and 7% (i.e. 2/28, of which both wounds showed clinical signs of clinical infection i.e. malodorous, slimy, pus) scored 2.0 ng/ml. The PCT concentrations in horses with chronic or acute wounds were compared as seen in Table 2.

TABLE 1

Case information and PCT results from wound exudates tested immediately after collection.

| BREED | SEX | AGE (YRS) | TYPE OF WOUND | CLINICAL SIGNS OF INFECTION | PCT RESULT ng/ml |
|---|---|---|---|---|---|
| T. B. Bay | Filly | 1 | Trauma wound L. hind dorsal, just below the knee—3 week old wound | ND | <0.5 |
| Welsh X | Colt | 2 | Trauma wound | ND | <0.5 |
| Welsh | Mare | 5 | Trauma wound | ND | <0.5 |
| Hunter | Gelding | 6 | Trauma/wire | ND | <0.5 |
| Arab | Gelding | 2 | Burn | Infected—inflamed, exuding, very malodourous, slimy | >2.0 |
| Cob | Gelding | 10 | Open chest wound | A lot of pus draining, no malodour | <0.5 |
| Warmblood | Gelding | 8 | Surgical wound infection | ND | Not tested Sample too viscous. |
| Thoroughbred | Mare | 3 | Hock wound euthanized due to infection | ND | Not tested Sample too viscous. |
| Cob | Gelding | 12 | Surgical wound infection | Pus present along the edge of the wound | Negative result |
| Warmblood | Gelding | 6 | Open draining wound | Pus present along the edge of the wound | Negative result |
| Thoroughbred | Mare | 12 | Trauma wound | ND | Negative result |

ND = not determined.

TABLE 2

Case information and PCT results from wound exudates tested after collection and being stored at −20° C.

| BREED | SEX | AGE (YRS) | TYPE OF WOUND | CLINICAL SIGNS OF INFECTION | PCT result ng/ml |
|---|---|---|---|---|---|
| TB Bay | Filly | 1 | Trauma wound L. hind dorsal, just below the knee, 3 week wound | Slimy malodourous | 0.5 |
| TB | Gelding | 16 | Trauma wound heel bulb 15 days old | Slimy malodourous | 0.5 |
| Unknown | Mare | 5 | Colic case abdominal wound | ND | 0.5 |
| TB Bay | Gelding | 4 | Trauma shoulder wound 8-9 days old | ND | 0.5 |
| WBxTB | Mare | 7 | Trauma wound wire injury to hock | ND | 0.5 |
| TB | Mare | 6 | Trauma wound | ND | <0.5 |
| TB | Gelding | 7 | Trauma wound | ND | <0.5 |
| Cob | Mare | 9 | Trauma wound | ND | <0.5 |
| TB | Filly | 3 | Trauma wound fetlock | ND | 0 |
| British Warm Blood | Mare | 5 | Trauma wound to limb 5 days old | ND | 0 |
| TBx | Geldng | 4 | Trauma wound | ND | 0 |
| Cob | Mare | 19 | Hind fetlock trauma wound 24 hours old | ND | 0 |
| TB | Filly | 2 | Trauma wound fetlock | ND | 0 |
| Arab | Colt | 2 | Trauma wound | ND | 0 |
| TB | Gelding | 6 | Trauma wound | ND | 0 |
| Anglo Arab | Mare | 5 | Trauma wound point of hock | ND | 0 |
| TBx | Mare | 16 | Trauma hock wound | Sepsis, pus, malodourous | >2.0 |

These results show that procalcitonin in wound exudate is able to determine infection status in acute and chronic wounds. This can be seen by the correlation between higher exudate PCT levels and signs of infection in a variety of wounds. For example a clear correlation can be seen between a PCT level of >2 and clinical signs of infection. The results also show that freezing the samples does not affect the result from the test.

EXAMPLE 3

Wound fluid samples were collected from human chronic wounds and assessed for evidence of procalcitonin using the PCT-Q kit (BRAHMS, Germany). In most cases, wound fluid samples were diluted (1:5 or 1:10) because the samples were too viscous to measure using the PCT-Q lateral flow system.

In one patient (016), a leg ulcer of 3 years duration was considered to be clinically infected. There was also evidence of biofilm and exudate level was heavy. Procalcitonin detection using the PCT-Q kit indicated a level of >0.5 ng/ml.

A second patient (018) had a leg ulcer of 4 years duration, with heavy exudate level and evidence of biofilm. Procalcitonin detection using the PCT-Q kit indicated a level of 0.5 ng/ml.

A third patient (019) had a pressure ulcer of 5 years duration, with heavy exudate level and evidence of biofilm. Procalcitonin detection using the PCT-Q kit was negative (i.e. <0.5 ng/ml).

A negative control sample using horse serum produced a negative result in the PCT-Q kit (i.e. <0.5 nh/ml).

Data generated from the three clinical cases indicate a potential correlation between procalcitonin level in wound exudate and infection status in chronic wounds.

The invention claimed is:

1. A method of diagnosis and treatment of a local bacterial infection in a wound of a mammal, the method comprising:
   obtaining fluid from the wound of the mammal;
   detecting a procalcitonin level in the fluid from the wound of the mammal that is at least equal to or greater than 0.5 ng/ml by observing an appearance of an indicator on a device, wherein the procalcitonin level of at least equal to or greater than 0.5 ng/ml in the fluid from the wound of the mammal is indicative of the local bacterial infection in the wound, and wherein the device is configured such that the indicator appears in the presence of the procalcitonin level of at least equal to or greater than 0.5 ng/ml in the fluid from the wound and the indicator does not appear in the presence of a procalcitonin level of less than 0.5 ng/ml in the fluid from the wound; and
   administering local and systemic antimicrobial therapy to the mammal to reduce or eliminate the local bacterial infection in the wound of the mammal in response to detecting the procalcitonin level of at least equal to or greater than 0.5 ng/ml.

2. The method as claimed in claim 1 wherein the detecting is carried out in vitro on the fluid from the wound.

3. The method as claimed in claim 1 further comprising comparing a measured procalcitonin level with a reference procalcitonin level characteristic of a non-infected wound.

4. The method as claimed in claim 1 further comprising diluting the fluid from the wound.

5. The method as claimed in claim 1 wherein the wound is a chronic wound.

6. The method as claimed in claim 5 wherein the chronic wound is selected from the group consisting of a pressure ulcer, a leg ulcer, a trauma wound, a surgical wound and a burn wound.

7. The method as claimed in claim 1 wherein the procalcitonin level of at least equal to or greater than 0.5 ng/ml is detected in the fluid by using a binding partner.

8. A method of diagnosis and treatment of a local bacterial infection in a wound of a subject, the method comprising:
   obtaining a sample from the subject, wherein the sample comprises fluid taken from the wound;
   detecting a procalcitonin level in the fluid taken from the wound that is at least equal to or greater than 0.5 ng/ml by observing an appearance of an indicator on a device, wherein the device is configured such that the indicator appears in the presence of the procalcitonin level of at least equal to or greater than 0.5 ng/ml in the fluid from the wound and the indicator does not appear in the presence of a procalcitonin level of less than 0.5 ng/ml in the fluid from the wound, and wherein the device includes a first reference band indicative of a first procalcitonin level that is less 0.5 ng/ml, a second reference band indicative of a second procalcitonin level that is greater than or equal to 0.5 ng/ml, a third reference band indicative of a third procalcitonin level that is equal to or greater than 2.0 ng/ml, and a fourth reference band indicative of a fourth procalcitonin level that is equal to or greater than 10.0 ng/ml;
   diagnosing the local bacterial infection in the wound in response to detecting the procalcitonin level of at least equal to or greater than 0.5 ng/ml; and
   administering a local and systemic antimicrobial therapy to the subject in response to diagnosing the local bacteria infection in the wound.

9. The method of claim 8, wherein the device includes a pipette, a lateral flow test strip, and a color scale.

10. The method of claim 8, wherein the device includes a test strip in the form of a dip stick and a color scale.

11. The method of claim 8, wherein obtaining the sample includes obtaining 200 microliters of fluid taken from the wound.

12. The method of claim 11, further comprising applying the 200 microliters of fluid taken from the wound onto the device.

13. The method of claim 12, wherein detecting the procalcitonin level of at least equal to or greater than 0.5 ng/ml in the fluid from the wound includes detecting the procalcitonin level of at least equal to or greater than 0.5 ng/ml in the fluid from the wound subsequent to applying the 200 microliters of fluid taken from the wound onto the device.

14. The method of claim 12, wherein applying the 200 microliters of fluid taken from the wound onto the device includes incubating the 200 microliters of fluid taken from the wound at room temperature for 30 minutes.

15. The method of claim 8, wherein the fluid taken from the wound is substantially devoid of blood or tissue plasma remote from a site of the wound.

16. A method of diagnosis and treatment of a local bacterial infection in a wound of a subject, the method comprising:
   applying a device to the wound that includes a binding partner to bind with procalcitonin present in fluid from the wound;
   obtaining a sample from the subject by the device, wherein the sample comprises fluid from the wound that is substantially devoid of blood or tissue plasma remote from a site of the wound;
   detecting a procalcitonin level in the fluid taken from the wound that is at least equal to or greater than 0.5 ng/ml by observing an appearance of an indicator on the device, wherein the device is configured such that the indicator appears in the presence of the procalcitonin level of at least equal to or greater than 0.5 ng/ml in the fluid from the wound and the indicator does not appear in the presence of a procalcitonin level less than 0.5 ng/ml in the fluid from the wound, and wherein the device includes a first color marker indicative of a first procalcitonin level that is less 0.5 ng/ml, a second color marker indicative of a second procalcitonin level that is greater than or equal to 0.5 ng/ml, a third color marker indicative of a third procalcitonin level that is equal to or greater than 2.0 ng/ml, and a fourth color marker indicative of a fourth procalcitonin level that is equal to or greater than 10.0 ng/ml;
   diagnosing the local bacterial infection in the wound in response to detecting the procalcitonin level of at least equal to or greater than 0.5 ng/ml; and
   administering a local and systemic antimicrobial therapy to the subject in response to diagnosing the local bacteria infection in the wound.

17. The method of claim 16, wherein the device is a wound dressing.

18. The method of claim 16, wherein obtaining the sample from the subject by the device includes absorbing 200 microliters of fluid from the wound by the device.

19. The method of claim 16, wherein diagnosing the local bacterial infection in the wound includes detecting one of the second, third, and fourth color markers of the device.

20. The method of claim 19, wherein diagnosing the local bacterial infection in the wound includes detecting one of the third and fourth color markers of the device.

* * * * *